US00PP33379P2

(12) United States Plant Patent
Kerley et al.

(10) Patent No.: US PP33,379 P2
(45) Date of Patent: Aug. 17, 2021

(54) ***PETUNIA* 'KERPRILPRO'**

(50) Latin Name: *Petunia atkinsiana*
Varietal Denomination: KERPRILPRO

(71) Applicants: Timothy Kerley, Cambridge (GB); Sarah Kerley, Cambridge (GB); David Kerley, Cambridge (GB); Priscilla Kerley, Cambridge (GB)

(72) Inventors: Timothy Kerley, Cambridge (GB); Sarah Kerley, Cambridge (GB); David Kerley, Cambridge (GB); Priscilla Kerley, Cambridge (GB)

( * ) Notice: Subject to any disclaimer, the term of this patent is extended or adjusted under 35 U.S.C. 154(b) by 0 days.

(21) Appl. No.: 17/109,552

(22) Filed: Dec. 2, 2020

(51) Int. Cl.
*A01H 6/52* (2018.01)
*A01H 5/02* (2018.01)

(52) U.S. Cl.
USPC ..... Plt./356.13

(58) Field of Classification Search
USPC ..... Plt./356.13
See application file for complete search history.

*Primary Examiner* — Annette H Para
(74) *Attorney, Agent, or Firm* — Cassandra Bright

(57) ABSTRACT

A new and distinct *Petunia* cultivar named 'KERPRILPRO' is disclosed, characterized by a dense, spreading growth habit, and attractive double violet flowers with darker violet veins. The plants flower freely and begin flowering under short day condition. The new variety is a *Petunia*, normally produced as an outdoor garden or container plant.

2 Drawing Sheets

Figure 1:
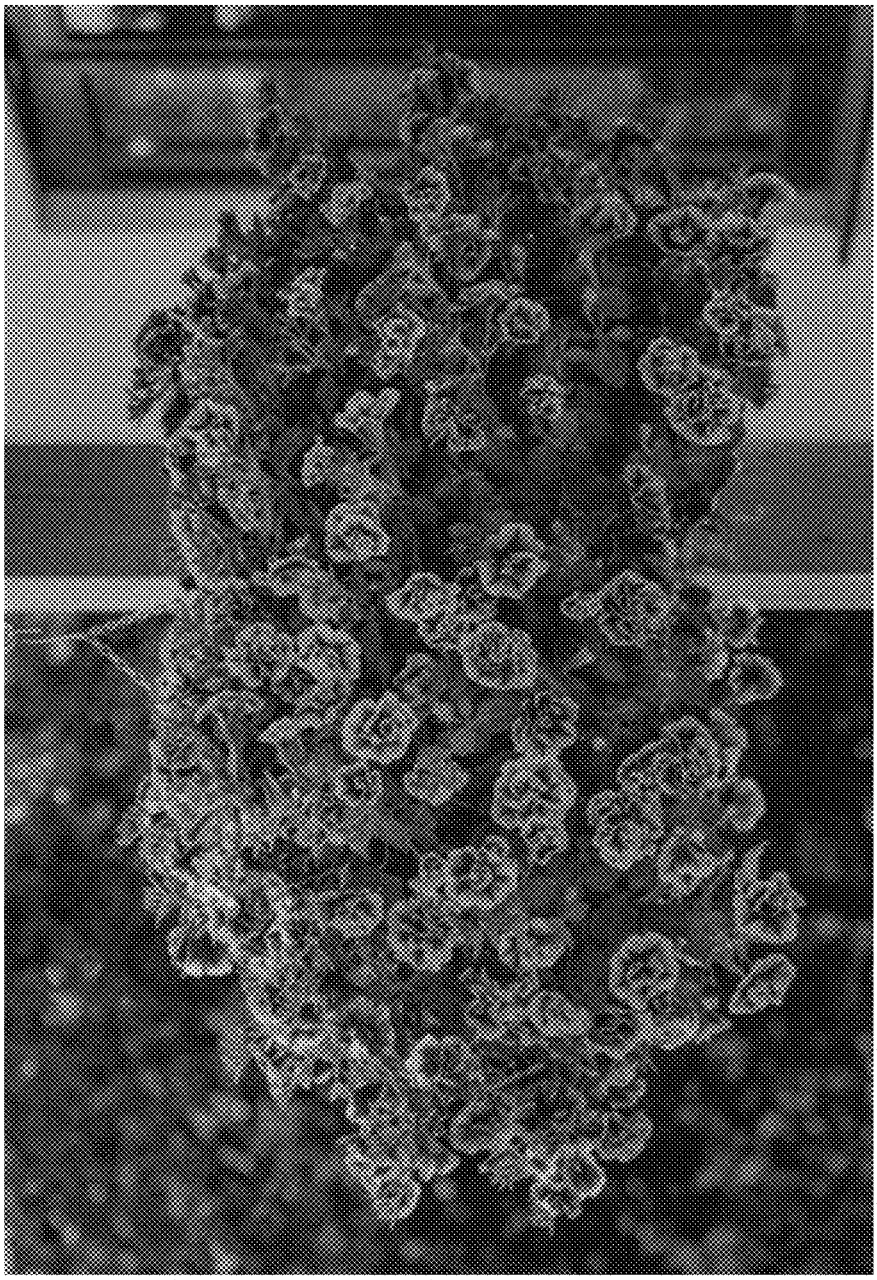

Latin name of the genus and species: *Petunia atkinsiana*.
Variety denomination: 'KERPRILPRO'.

BACKGROUND OF THE INVENTION

'KERPRILPRO' is a product of a breeding and selection program for ornamental *Petunia* varieties to be vegetatively propagated. The new plant of the present invention comprises a new and distinct cultivar of *Petunia* plant.

'KERPRILPRO' is a seedling resulting from the crossing of an, unpatented proprietary *Petunia atkinsiana* referred to as '15-930-2' with the pollen parent, an unpatented, proprietary, *Petunia atkinsiana* referred to as '15-930-6', conducted in August 2015. The selection of the new variety was made in May 2016, by the inventor at a research greenhouse located in Cambridge, UK.

'KERPRILPRO' was first asexually reproduced by vegetative terminal cuttings at a research greenhouse in Cambridge, UK, September 2016. The new cultivar has been found to retain its distinctive characteristics through successive asexual propagations.

SUMMARY OF THE INVENTION

The cultivar 'KERPRILPRO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERPRILPRO' These characteristics in combination distinguish 'KERPRILPRO' as a new and distinct *Petunia* cultivar:

1. Attractive double flowers
2. Day-length neutral flowering. Flower bud initiation occurs in day lengths of less than 8 hours.
3. Spreading plant habit.
4. Violet flower with dense, dark violet colored veins.

5. Abundant flowering.
6. Light floral fragrance.

PARENT COMPARISON

Plants of the new cultivar 'KERPRILPRO' are similar to plants of the seed parent in most horticultural characteristics, however, plants of the new cultivar 'KERPRILPRO' differ in the following:

1. 'KERPRILPRO' flowers more abundantly than the seed parent.
2. The new variety produces double flowers; the seed parent produces single flowers.
3. The new variety has shorter lateral branches than the seed parent.

Plants of the new cultivar 'KERPRILPRO' are similar to plants of the pollen parent in most horticultural characteristics however, plants of the new cultivar 'KERPRILPRO' differ in the following:

1. 'KERPRILPRO' is a low, spreading plant, the pollen parent has an upright habit.

COMMERCIAL COMPARISON

Plants of the new cultivar 'KERPRILPRO' can be compared to the commercial variety *Petunia* 'Kerprilcomp', U.S. Plant Pat. No. 19,327. These varieties are similar in most horticultural characteristics, having fully double flowers and distinctive dark flower veins. The new variety 'KERPRILPRO', however, differs in the following:

1. 'KERPRILPRO' has a violet flower with dark violet veins, this comparator has a purple flower with dark purple veins.
2. 'KERPRILPRO' flowers more abundantly than this comparator.
3. 'KERPRILPRO' begins flowering earlier than this comparator.

4. 'KERPRILPRO' produces more branches than this comparator.

Plants of the new cultivar 'KERPRILPRO' can also be compared to the commercial variety *Petunia* 'Tumbelina Priscilla', unpatented. These varieties are similar in most horticultural characteristics, having double flowers and compact plant forms. 'KERPRILPRO' however, differs in the following:

1. 'KERPRILPRO' flowers more abundantly.
2. 'KERPRILPRO' has a smaller flower.
3. 'KERPRILPRO' has more petals in the flower.
4. Tumbelina Priscilla has veins colored N82A; the new variety has veins colored Violet 86A and 86B.
5. 'KERPRILPRO' has a more stable flower color.
6. 'KERPRILPRO' flowers earlier and in short days.

BRIEF DESCRIPTION OF THE PHOTOGRAPHS

The accompanying photograph in FIG. 1 illustrates in full color a typical plant of 'KERPRILPRO' grown in a greenhouse, in Cambridge, United Kingdom.

Figure 2:
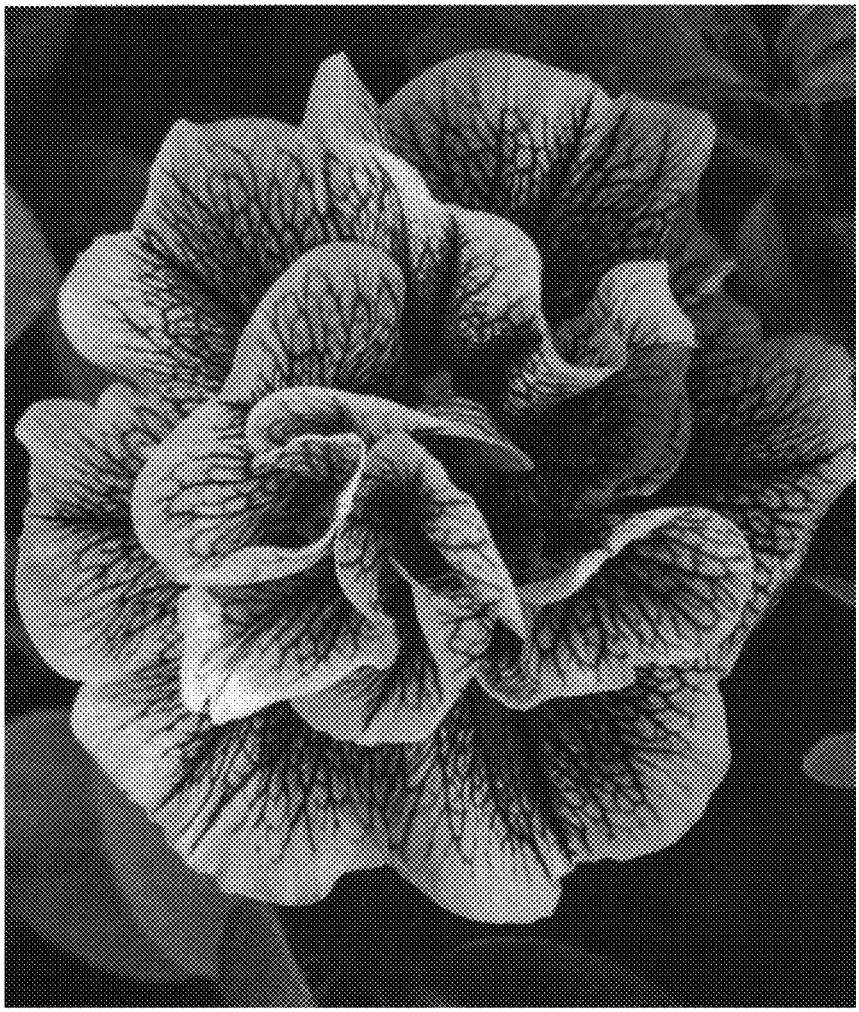

FIG. 2 illustrates in full color a typical mature flower of 'KERPRILPRO' during Spring. Age of the plant photographed is approximately 90 days from a rooted cutting in a 20 cm basket.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KERPRILPRO' plants grown in greenhouse in Cambridge, United Kingdom, under natural lighting. Measurements were taken during April of 2018. The plants were approximately 16 weeks old from a rooted cutting in a 20 cm basket. The growing temperature ranged from 20° C. to 35° C. during the days, 17° C. to 23° C. during the nights. Measurements and numerical values represent averages of typical plant types.

Botanical classification: *Petunia atkinsiana* 'KERPRILPRO'.

PROPAGATION

Time to initiate roots: Approximately 10 days at 20° C.
Root description: Fibrous, freely branching. White, to light tan, not accurately measured with R.H.S. chart.
Time to produce a rooted cutting: About 21 to 28 days.

PLANT

Growth habit: Spreading and dense.
Pot size of plant described: 12.7 cm basket.
Height: 58.0 cm to top of flowering plane.
Plant spread: 37.0 cm.
Growth rate: Moderate
Length of primary lateral branches: 22.7 cm.
Diameter of lateral branches: 0.4 cm.
Quantity of primary lateral branches: 5.
Characteristics of primary lateral branches:
- *Color.*—Young stem: RHS Yellow-Green 146C. Mature stem: RHS Yellow-Green 146B.
- *Texture.*—Densely pubescent.
- *Strength.*—Strong.

Internode length: 2.8 cm.

FOLIAGE

Leaf:
- *Arrangement.*—Alternate before flowering, then opposite.
- *Form.*—Simple.
- *Quantity.*—23 per main branch.
- *Average length.*—5.5 cm.
- *Average width.*—4.4 cm.
- *Shape of blade.*—Ovate.
- *Apex.*—Acute.
- *Base.*—Obtuse.
- *Margin.*—Entire.
- *Angle of attachment.*—About 90 degrees from stem. Slightly reflexing back with age.
- *Texture of top surface.*—Sparsely pubescent.
- *Texture of bottom surface.*—Sparsely pubescent.
- *Color.*—Young foliage upper side: Near RHS Yellow-Green 146A. Young foliage under side: RHS Yellow-Green 146B. Mature foliage upper side: RHS Green N137B. Mature foliage under side: RHS Yellow-Green 146B.
- *Venation.*—Type: Pinnate. Venation color upper side: RHS Yellow-Green 146D. Venation color under side: RHS Yellow-Green 146C.
- *Petiole.*—Length: 1.1 cm. Diameter: 0.2 cm. Color: RHS Yellow-Green 146C. Texture: Pubescent.

FLOWER

Natural flowering season: Spring and Summer in Cambridge, United Kingdom.
Days to flowering from rooted cutting: 21 to 28 days.
Inflorescence and flower type and habit: Double, facing outwards and upwards.
Rate of flower opening: About 2-3 days from bud to fully opened flower.
Flower longevity on plant: 10 to 12 days.
Approximate quantity of flowers per plant: Average 30 flowers on a plant of this age.
Persistent or self-cleaning: Self-cleaning.
Bud:
- *Shape.*—Conical.
- *Length.*—3.2 cm.
- *Diameter at apex.*—1.1 cm.
- *Diameter at base.*—0.5 cm.
- *Texture.*—Densely pubescent, especially along midveins.
- *Color.*—RHS Greyed-Purple N186B with a flush of Violet 86B and White 155A toward apex. Base/outer tube Greyed-Purple N187A streaked Greyed-Green 194A.

Flower size:
- *Diameter.*—7 cm.
- *Length.*—About 3.3 cm.
- *Flower tube diameter at distal end.*—About 1.7 cm.
- *Flower tube diameter at proximal end.*—About 0.5 cm.

Petals:
- *Length from tube.*—2.7 cm.
- *Length of free portion.*—1.6 cm.
- *Width.*—3.4 cm.

*Quantity.*—18.
*Shape.*—Cuneate.
*Appearance.*—Matte.
*Texture, upper surface.*—Glabrous.
*Texture, lower surface.*—Slightly pubescent, mainly on veins.
*Apex.*—Retuse.
*Margin.*—Entire, ruffled. Interior petals more ruffled.
*Lobing.*—Very weak to absent.

Color:
*When opening.*—
*Upper surface.*—Near Violet 86A, marginal region near 86B, then 87D at outermost.
*Lower surface.*—Near Violet 86D with dense veining of 86A.
*Fully opened.*—
*Upper surface.*—Coloration mainly from veins, near Violet 86A and 86B, outer edge 84D.
*Lower surface.*—Near Violet 86B at base, changing to 85C with veins 86B.
*Flower throat (inside).*—RHS Greyed-Purple N186A.
*Flower throat, vein.*—Not distinguishable from surface color.
*Flower tube (outside).*—RHS Greyed-Purple N187B.
*Flower tube, vein (outside).*—RHS Greyed-Purple N187B.

Corolla tube:
*Length.*—3.1 cm.
*Diameter at distal end.*—1.7 cm.
*Diameter at proximal end.*—0.5 cm.
*Texture, inner surface.*—Glabrous.
*Texture, outer surface.*—Densely pubescent.

Sepals:
*Quantity per flower.*—5 fused along lower half.
*Shape.*—Cuneate.
*Length.*—1.3 cm.
*Width.*—0.5 cm.
*Margin.*—Entire.
*Apex.*—Acute.
*Texture, lower surfaces.*—Pubescent.
*Texture, upper surfaces.*—Pubescent.
*Color.*—Upper Surface: Near RHS Green 137B. Lower Surface: Near RHS Green 137B.

Peduncle:
*Strength.*—Moderate.
*Aspect.*—45 degrees to stem, varying to about 90 degrees with age.
*Length.*—4.1 cm.
*Diameter.*—2 mm.
*Texture.*—Densely pubescent.
*Color.*—Near RHS Yellow-Green 146B.

Fragrance: Light floral fragrance.

REPRODUCTIVE ORGANS

Stamens:
*Number.*—Average range 4 to 8.
*Length.*—2.0 cm
*Filament length.*—1.3 cm.
*Filament color.*—RHS Greyed-Green 196A.

Anthers:
*Length.*—2 mm.
*Shape.*—Reniform.
*Color.*—Near RHS Violet-Blue 97B.
*Pollen.*—Color: Near RHS Violet-Blue 98D.

Pistil:
*Number.*—0 or 1, not always present.
*Length.*—2.3 cm.
*Style.*—Length: 1.7 cm. Color: RHS Greyed-Green 193A.
*Stigma.*—Shape: Linear. Color: RHS Greyed-Purple 187A. Ovary Color: RHS Green 143C.

OTHER CHARACTERISTICS

Seeds and fruits: Not observed to date.

Disease/pest resistance: Neither resistance nor susceptibility to the normal diseases and pests of *Petunia* have been observed. Typical well-known diseases include: *Botrytis cineria, Fusarium, Pythium, Phytophthora*, and *Rhizoctonia* species. Typical well-known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'KERPRILPRO' as herein illustrated and described.

* * * * *